(12) United States Patent
Hartley et al.

(10) Patent No.: US 8,747,449 B2
(45) Date of Patent: Jun. 10, 2014

(54) ENDOSCOPIC DELIVERY DEVICE

(75) Inventors: David Ernest Hartley, Wannanup (AU); Michael Lawrence-Brown, City Beach (AU); Shirley Jansen, West Perth (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/209,856

(22) Filed: Aug. 15, 2011

(65) Prior Publication Data

US 2011/0306914 A1    Dec. 15, 2011

Related U.S. Application Data

(62) Division of application No. 12/011,887, filed on Jan. 30, 2008, now Pat. No. 8,034,093.

(60) Provisional application No. 60/898,604, filed on Jan. 31, 2007.

(51) Int. Cl.
*A61F 2/06* (2013.01)
*A61B 17/08* (2006.01)

(52) U.S. Cl.
USPC .......................................... 623/1.13; 606/153

(58) Field of Classification Search
USPC ................ 606/108, 198, 194; 623/23.7, 1.11, 623/1.12, 1.23, 1.13; 128/897, 898, 899
See application file for complete search history.

(56) References Cited

U.S. PATENT DOCUMENTS

| | | | |
|---|---|---|---|
| 5,941,908 A * | 8/1999 | Goldsteen et al. | 623/1.23 |
| 6,241,741 B1 | 6/2001 | Duhaylongsod et al. | |
| 6,966,887 B1 | 11/2005 | Chin | |
| 8,034,093 B2 * | 10/2011 | Hartley et al. | 623/1.11 |
| 2003/0212450 A1 * | 11/2003 | Schlick | 623/1.15 |
| 2005/0033418 A1 * | 2/2005 | Banas et al. | 623/1.49 |
| 2005/0125050 A1 | 6/2005 | Carter et al. | |
| 2006/0004433 A1 * | 1/2006 | Greenberg et al. | 623/1.11 |
| 2006/0149349 A1 * | 7/2006 | Garbe | 623/1.11 |

FOREIGN PATENT DOCUMENTS

| | | | |
|---|---|---|---|
| EP | 0732087 | | 9/1996 |
| EP | 0791332 | | 8/1997 |
| EP | 1790296 | | 5/2007 |
| WO | 96/14028 | | 5/1996 |
| WO | 96/24306 | | 8/1996 |
| WO | WO 2006/102020 | * | 9/2006 ................... 623/1.11 |

OTHER PUBLICATIONS

International Search Report, PCT/US2008/001229, William A. Cook Australia Pty. Ltd., Oct. 17, 2008.
Written Opinion, PCT/US2008/001229, William A. Cook Australia Pty. Ltd., Oct. 17, 2008.

* cited by examiner

*Primary Examiner* — Tuan V Nguyen
(74) *Attorney, Agent, or Firm* — Richard J. Godlewski

(57) ABSTRACT

An endoscopic or laparoscopic conduit delivery device (1) comprises first and second separately manipulable introducers (3, 5) with a laparoscopic conduit (80) having first and second ends (83, 84) and an intermediate portion being mounted onto the introducers in a substantially U shape. The first end and a first portion of the laparoscopic conduit is retained onto the first introducer and the second end and a second portion of the laparoscopic conduit is retained on the second introducer and the intermediate portion extends between the first and second introducers. A main sheath (42) is over the first and second introducers. The endoscopic or laparoscopic conduit delivery device is introduced to a body cavity through an endoscopic or laparoscopic port (50).

9 Claims, 18 Drawing Sheets

ENDOSCOPIC DELIVERY DEVICE

CROSS-REFERENCE TO RELATED APPLICATIONS

This application is a divisional application that claims the benefit of priority under 35 U.S.C. §121 of U.S. patent application Ser. No. 12/011,887, filed Jan. 30, 2008, which is U.S. Pat. No. 8,034,093, which claims priority to U.S. Provisional Application Ser. No. 60/898,604, filed Jan. 31, 2007, which is hereby incorporated by reference in its entirety.

TECHNICAL FIELD

This invention relates to a medical device and more particularly to a device suitable for endoscopic delivery of a vascular conduit into the human or animal body.

BACKGROUND OF THE INVENTION

It is known to provide a bypass for damaged parts of vessels of the human or animal body using open surgical techniques and conventional sewn anastomoses. It would be an advantage if such operations could be carried out without the necessity of performing open surgery as considerably reduced hospital stays and costs would be involved.
It is also known to use endovascular techniques to deploy a stent graft in the human or animal body to span a damaged portion of the vasculature. There may be situations, however, where the vessel to be repaired is not accessible by endovascular techniques due to the particular vascular configuration, occlusions or vascular damage.

SUMMARY OF THE INVENTION

The present invention seeks to provide an alternative arrangement to known systems for performing vascular repair.

According to an aspect of the present invention, there is provided a bypass conduit delivery device comprising: first and second separately manipulable introducers for carrying a bypass conduit provided with first and second ends and an intermediate portion, the bypass conduit being mountable onto the introducers in a substantially U shape with the first end and a first portion of the bypass conduit retained onto the first introducer and the second end and a second portion of the bypass conduit retained on the second introducer and the intermediate portion extending between the first and second introducers, and a main sheath over the first and second introducers.

Preferably the first and second introducers are arranged side by side.

The bypass conduit can include an aperture in the intermediate portion and a catheter of each of the first and second introducers passes through the aperture in the bypass conduit. Preferably the aperture in the bypass conduit is pre-stitched whereby to facilitate closure of the aperture after removal of the first and second introducers.

To facilitate deployment each of the first and second introducers can comprise a guide wire lumen therethrough.

In a preferred embodiment each the each of the first and second introducers includes a splittable sheath co-axially therearound to contain the first and second portions of the bypass conduit onto the first and second introducers respectively, each splittable sheath including an aperture to allow the intermediate portion of the bypass conduit to extend between the first introducer and the second introducer through the respective apertures in the sheath. A splittable sheath refers to a sheath with a pre-formed longitudinal groove which will assist with propagation of a split along the groove from the aperture in the sheath when a load is placed onto it.

Each of the first and second splittable sheaths can extend to a sheath manipulator and each sheath manipulator can include a haemostatic seal and the main sheath over the first and second introducers can also include a haemostatic seal.

Preferably each of the first and second introducers comprise a pusher catheter, a pusher lumen therethrough, a guide wire catheter extending through the pusher lumen and a nose cone dilator on the guide wire catheter.

The bypass conduit can comprise a tubular body of a biocompatible graft material and a plurality of self expanding stents along at least part of the length thereof. At least two of the plurality of self expanding stents at the first and second ends of the bypass conduit can be on the inside of the tubular body and the balance being on the outside of the tubular body and the bypass conduit can include a corrugated intermediate portion.

Alternatively the bypass conduit can comprise a tubular body of a biocompatible graft material which includes a corrugated intermediate portion and at least one balloon expandable stent at each end thereof. For this embodiment each of the first and second introducers can include an inflatable balloon to enable expansion of the balloon expandable stents.

The bypass conduit delivery device can further including a endoscopic access port which includes an access valve incorporating a haemostatic seal.

According to another aspect of the present invention, there is provided a bypass conduit for use in bypassing a patient's vasculature including: first and second ends and an intermediate portion, an aperture in the intermediate portion and at least one suture thread pre-sewn in a lose manner to the aperture, the bypass conduit being resiliently deformable to substantially a U-shape such that the aperture with the suture thread is open for the passage of introducer elements therethrough.

According to another aspect of the present invention, there is provided a bypass conduit delivery device in combination with a bypass conduit comprising; first and second separately manipulable introducers arranged side by side, a bypass conduit provided with first and second ends and an intermediate portion, the bypass conduit being mounted onto the introducers substantially in a U-shape with the first end and a first portion of the bypass conduit retained onto the first introducer and the second end and a second portion of the bypass conduit retained on the second introducer and the intermediate portion extending between the first and second introducers, an aperture in the intermediate portion, the first and second introducers passing through the aperture in the bypass conduit, each of the first and second introducers including a splittable sheath co-axially therearound to contain the first and second portions of the bypass conduit onto the first and second introducers respectively, each splittable sheath including an aperture to allow the intermediate portion of the bypass conduit to extend between the first introducer and the second introducer through the respective apertures in the sheath, each of the first and second splittable sheaths extending to a sheath manipulator and each sheath manipulator including a haemostatic seal, and a main sheath over the first and second introducers.

The bypass conduit is preferably a laparoscopic conduit.

Generally it will be seen that the purpose of this device is to provide a system for deploying a bypass tubular graft from one vascular vessel to another that can be inserted under vision using laparoscopic or endoscopic techniques. This is to avoid open surgical vessel exposure and conventional sewn anastomoses. An example would be to provide a bypass around an occluded, ligated, resected or absent segment of one vessel. An alternative could be used to enable a bypass to be inserted from one vessel to another.

Generally the laparoscopic conduit is loaded into the delivery system so that it can be inserted into a body cavity e.g the peritoneal or thoracic cavity through a single opening in the layers covering the cavity for instance the abdominal or thoracic wall using an existing endoscopic port or the endoscopic port described in the present specification.

The ends of the laparoscopic conduit are loaded separately into split sheaths that can be removed once the laparoscopic conduit end is placed in the target vessel at the desired location. The central portion of the laparoscopic conduit is flexible so that it may be doubled over in the loading and initial delivery and then straightened out when placed in the intended position. Each end of the laparoscopic conduit has at least one attachment stent for fixing the position of the laparoscopic conduit in the target vessels.

The ends of the laparoscopic conduit can then be introduced into spaced apart locations on the vessel using the Seldinger technique over a guide wire.

BRIEF DESCRIPTION OF THE DRAWING

Embodiments of the present invention are described below, by way of example only, with reference to the accompanying drawings, in which.

DETAILED DESCRIPTION

Throughout this specification the term distal with respect to a portion of the aorta, a deployment device or a prosthesis is used to denote the end of the aorta, deployment device or prosthesis further away in the direction of blood flow away from the heart and the term proximal is used to denote the portion of the aorta, deployment device or end of the prosthesis nearer to the heart. When applied to other vessels, similar terms such as caudal and cranial should be understood.

The term endoscopic refers generally to operations performed using an endoscope, that is a device used to provide access through a small aperture in a body wall into a body cavity. Laparoscopic refers to an endoscopic operation into the abdominal cavity and thoracoscopic refers to an endoscopic operation into the thoracic cavity. Throughout this specification the term laparoscopic will be used but the invention is not so limited and is intended to cover operations into other body cavities.

Figure 1:
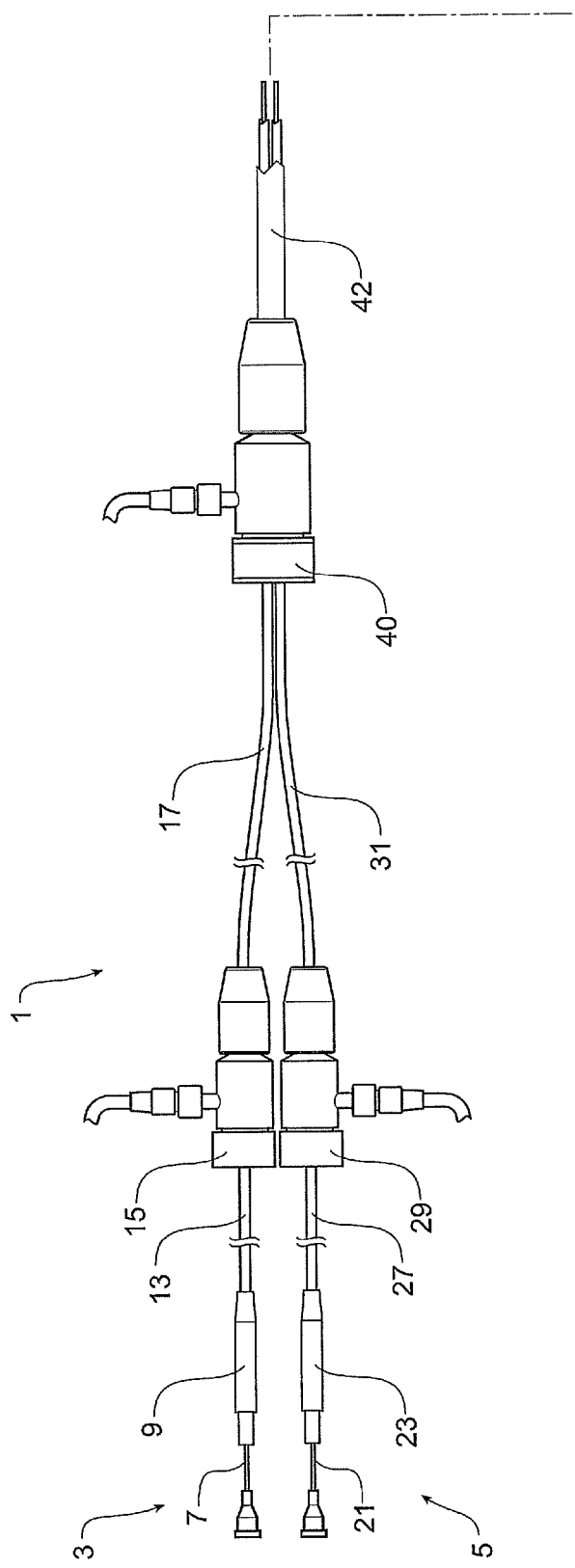
FIG. 1 shows a schematic view of a embodiment of a delivery device according to the present invention.
Figure 1:
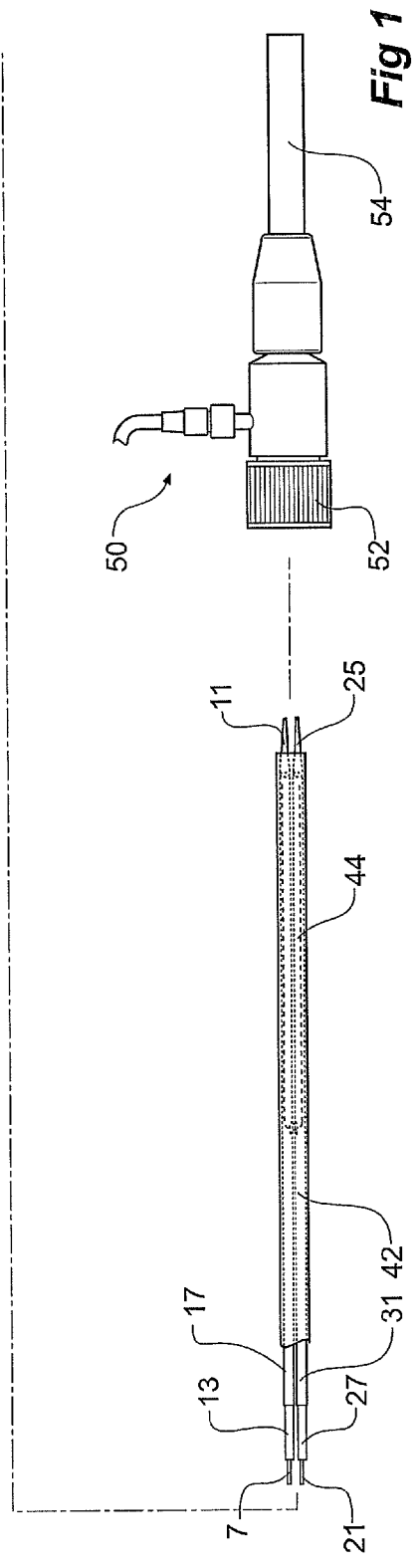

Now looking more closely at the drawings and in particular FIG. 1 an embodiment of a delivery device according to the present invention is illustrated.

In FIG. 1 the delivery device 1 has a first introducer 3 and a second introducer 5. The first introducer 3 has a first guide wire catheter 7 extending through a handle 9 at the distal end of the device 1 to a first introducer dilator or nose cone dilator 11 at the proximal end of the device. The first introducer 3 also includes a first pusher catheter 13 which extends from the handle 9 through a first hemostatic seal 15. A first inner sheath 17 extends from the hemostatic seal 15 to the first introducer dilator 11.

The second introducer 5 has a second guide wire catheter 21 extending through a handle 23 at the distal end of the device 1 to a second introducer dilator nose cone dilator 25 at the proximal end of the device. The first introducer 5 also includes a second pusher catheter 27 which extends from the handle 23 through a second hemostatic seal 29. A second inner sheath 31 extends from the hemostatic seal 29 to the second introducer dilator 25.

The first inner sheath 17 and the second inner sheath 31 together extend through an intermediate hemostatic valve 40. From the intermediate hemostatic valve 40 a middle sheath 42 extends proximally. The middle sheath 42 covers the first inner sheath 17 and the second inner sheath 31 and extends to the first and second dilators 11 and 25.

A laparoscopic conduit 44 is retained partly on the first introducer 3 and partly on the second introducer 5 just distal of the first introducer dilator 11 and second introducer dilator 25 such that the laparoscopic conduit is in a substantially "U" shape. More detail of the configuration of the proximal end of the introducer device is given in relation to FIGS. 6 and 7.

An endoscopic port 50 is used to enable introduction of the delivery device into a body cavity. The endoscopic port 50 has a valve 52 and an outer sheath 54 extending from the port.

Each of the hemostatic valves 15, 29, 40 and 52 may include a pair of silicone discs or similar with crossed slits so that a device can be introduced through the valve such that the silicone discs seal around the catheters introduced through the valve so as to prevent loss of blood or insufflation pressure within the body cavity. Additionally, one or more of hemostatic valves and, particularly endoscopic port valve 52, including a manually operable valve may be provided, the valve being openable so as to admit catheters or other instruments and closable around the catheters or other instruments. One such valve is a Captor Valve sold by Cook Incorporated (Bloomington Ind., USA).

Figures 2, 3A, 3B:
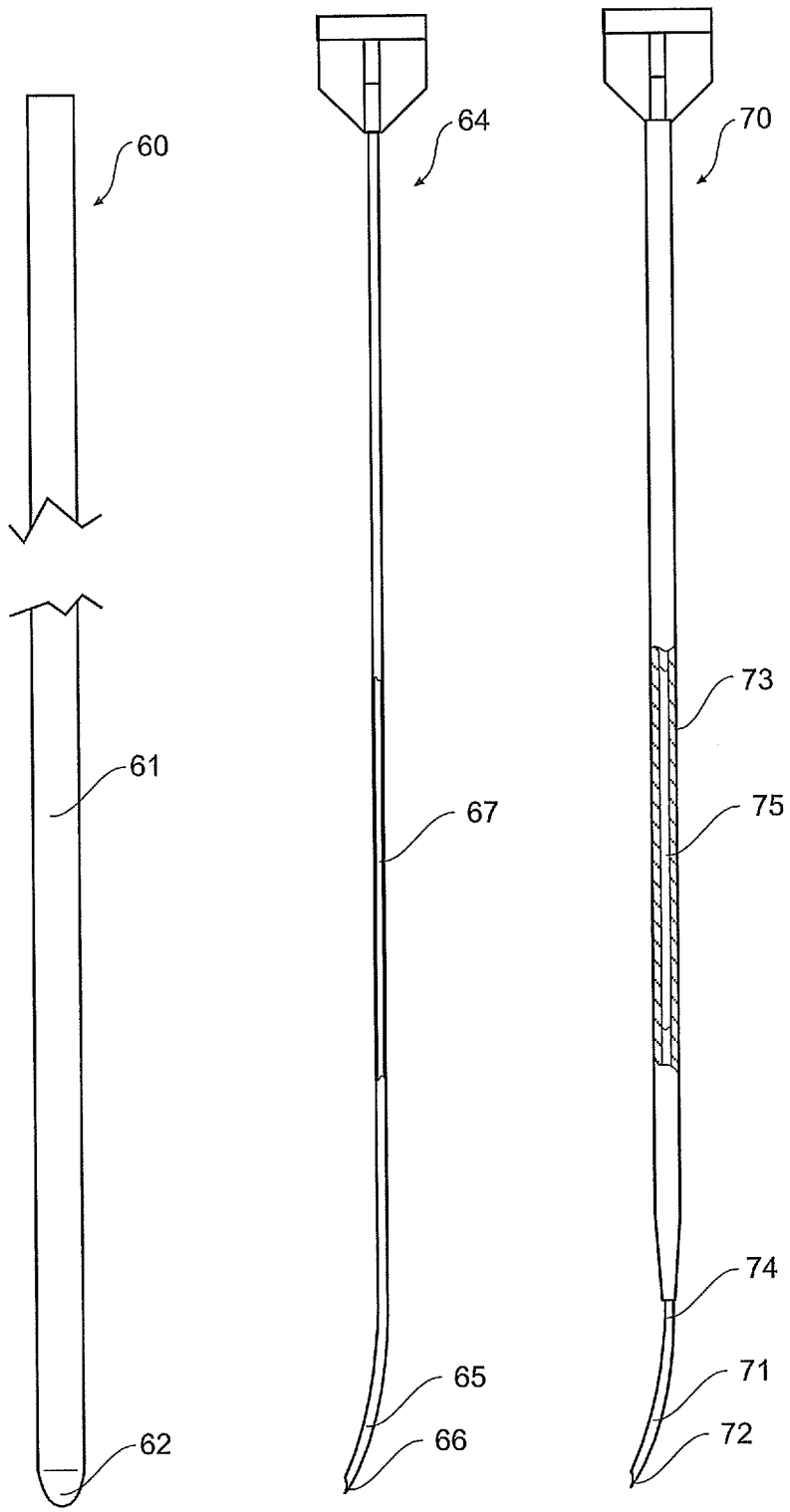
FIG. 2 shows a blunt obturator for use with the device of FIG. 1.
FIGS. 3A and 3B show curved needles suitable for use with the device of FIG. 1.

FIG. 2 shows a blunt obturator 60 which has an elongate body 61 and a blunt proximal end 62. The blunt obturator is used mounted into the endoscopic port 50 for pushing through a nick made in the body cavity wall such as the abdominal wall in an initial stage of a laparoscopic procedure. The blunt obturator is then removed, leaving the endoscopic port in place to provide an access path through the body cavity wall for deployment of the introducer taught herein. In one embodiment, the blunt obturator has a length of about 450 mm.

FIG. 3A shows one embodiment of a long, curved needle 64 suitable for passing through the endoscopic port after it has been deployed through the abdominal wall, as will be discussed in relation to FIG. 14. The curved needle 64 has a curved proximal end 65 with a sharpened tip 66 and a lumen 67 therein of sufficient size for the passage of a guide wire therethrough once access has been made into a vessel using the tip 66. The needle is shown partly in cutaway view to show the guide wire lumen 67 therewithin. In the embodiment shown, the elongate curved needle preferably is an 18 gauge needle with a lumen sufficient for a 0.9 mm (0.035") guide wire and has a length of about 320 mm. The lumen of the needle may have a diameter in the range of 0.35 mm to 1 mm (0.014" to 0.038"), that is suitable for all guide wires that could be potentially be used.

FIG. 3B shows another embodiment of a long, curved needle 70 suitable for passage through the laparoscopic port sheath after the latter has been deployed through the abdominal wall, as will be discussed in relation to FIG. 14. The curved needle 70 has a reinforcing body 73 around a catheter 74, with a curved proximal end 71 provided with a sharpened tip 72 and a lumen 75 therein of sufficient size for the passage of a guide wire therethrough once access has been made into a vessel using the tip 72. The curved needle 70 is shown partly in cutaway view to show the catheter 74 within the reinforced body and the guide wire lumen 75 through the catheter. The reinforcement body 73 extends along most of the needle and may terminate about 2 cm short of the tip and have a tapered proximal end. The reinforcement assists in providing rigidity to the needle when it is being forced into the aorta or other artery. In this example, the elongate curved needle is an 18 gauge needle with a lumen sufficient for a 0.9 mm (0.035") guide wire and has a length of about 320 mm. The reinforcing portion can have an outside diameter of about 3 mm. The lumen of the needle may have a diameter in the range of 0.35 mm to 1 mm (0.014" to 0.038"), that is suitable for all guide wires that could be potentially be used.

Figures 4, 4A:
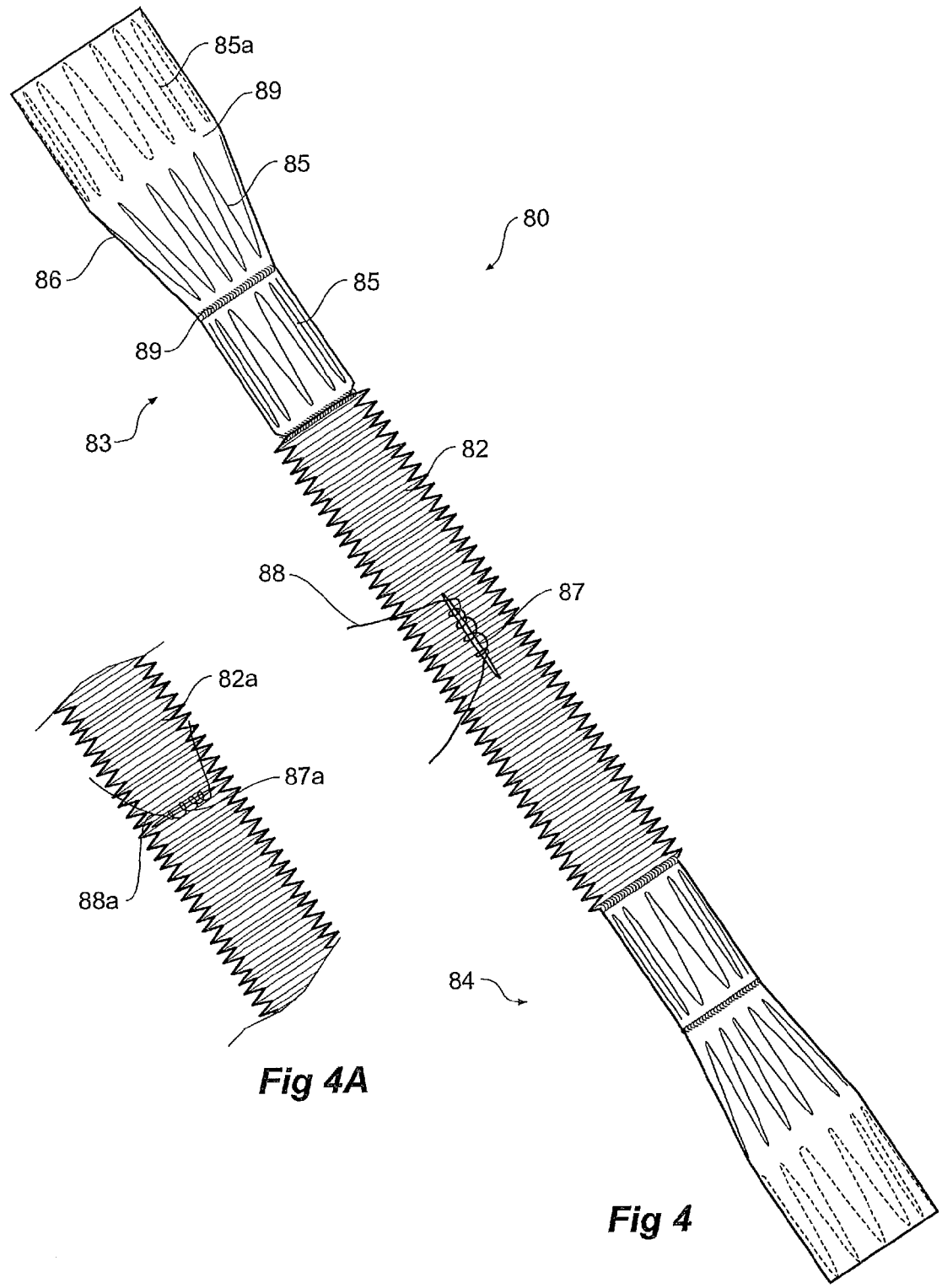
FIG. 4 shows a first embodiment of a laparoscopic conduit suitable for delivery using the delivery device of FIG. 1.

FIG. 4 shows a first embodiment of laparoscopic conduit suitable for delivery using the delivery device shown in FIG. 1. In this embodiment, the laparoscopic conduit 80 includes an elongate corrugated tubular body 82. At each end of the elongate corrugated tubular body there are connector portions 83 and 84 which is designed to be fitted into a vessel of the patient and to provide a fluid tight conduit exiting from the vessel at that point. The end 83 of the laparoscopic conduit comprises a tubular body of a biocompatible graft material 86 with a number of stents 85 supporting the tubular body. In this particular embodiment, although not strictly necessary, the stent 85a provided at the end of the tubular body is located inside the tubular body while the other stents 85 are on the outside thereof. This provides a smooth outside sealing surface at the end of the tubular body 82. Normally, the laparoscopic conduit would be deployed so that the vessel wall would extend around the tubular body in the zone 89 between the first and second stents 85, 85, or between the second and third stents 85, 85a to provide a seal. The end 84 of the laparoscopic conduit has a similar construction to the end 83. Intermediate the ends in the corrugated portion 82 there is provided is a longitudinal aperture 87 which can be closed off by means of pre-placed suture thread 88.

FIG. 4A shows a portion of another embodiment of a laparoscopic conduit which includes an elongate corrugated tubular body 82a. Intermediate the ends in the corrugated portion 82a there is provided a transverse aperture 87a which can be closed off by means of pre-placed stitching 88a.

Figure 5:
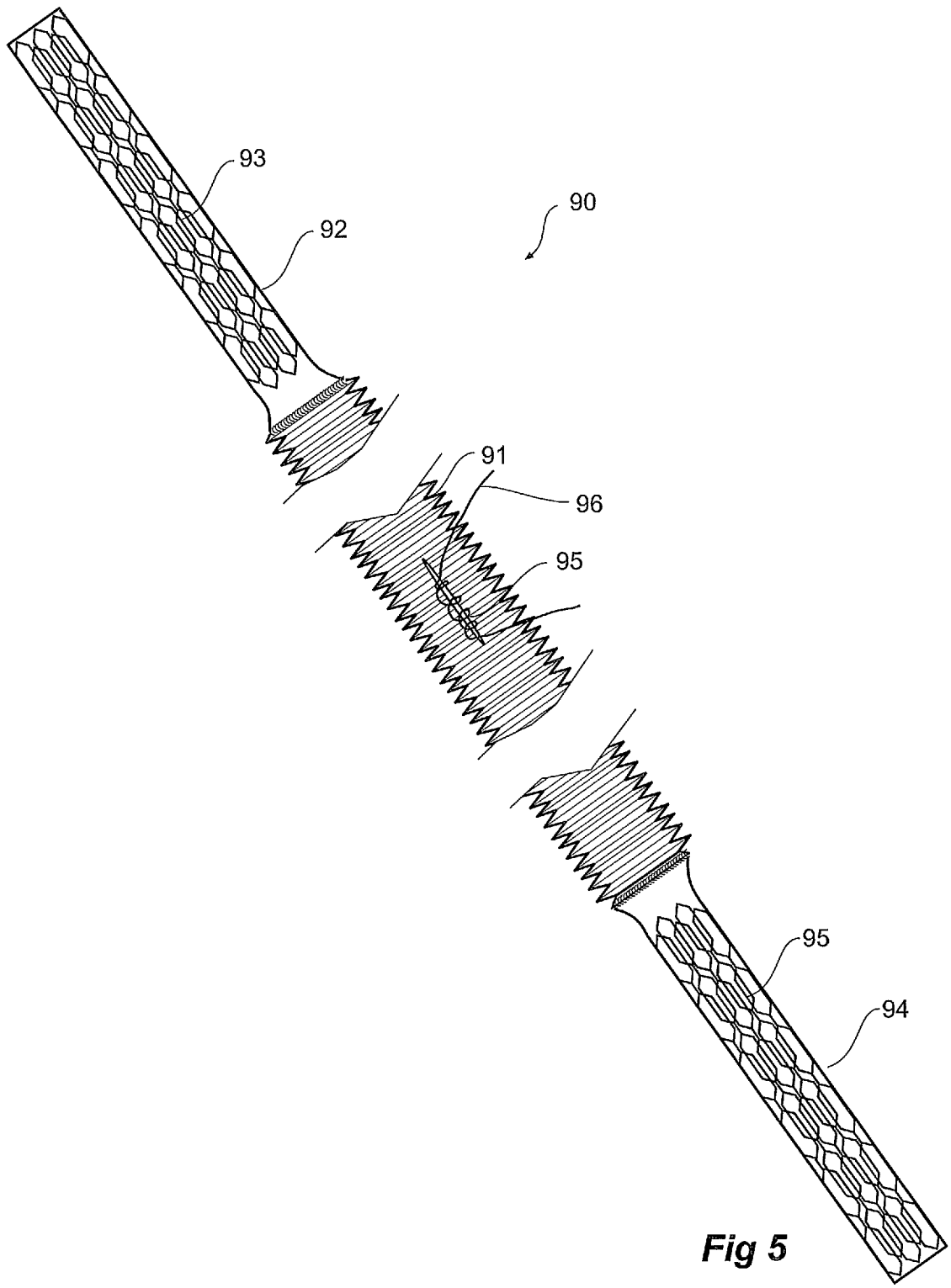
FIG. 5 shows another embodiment of a laparoscopic conduit suitable for delivery using the delivery device of FIG. 1.

FIG. 5 shows another embodiment of a laparoscopic conduit for delivery using the delivery device of FIG. 1. In this embodiment the conduit 90 consists of a corrugated tubular body 91 with tubular portions 92 and 94 of a biocompatible graft material extending from each end. The tubular portions 92 and 94 each have at least one balloon expandable stent 93 and 95 associated with the tubular end. Intermediate the ends in the corrugated portion there is provided an aperture 95 which can be closed off by means of pre-placed suture thread 96.

Figure 6:
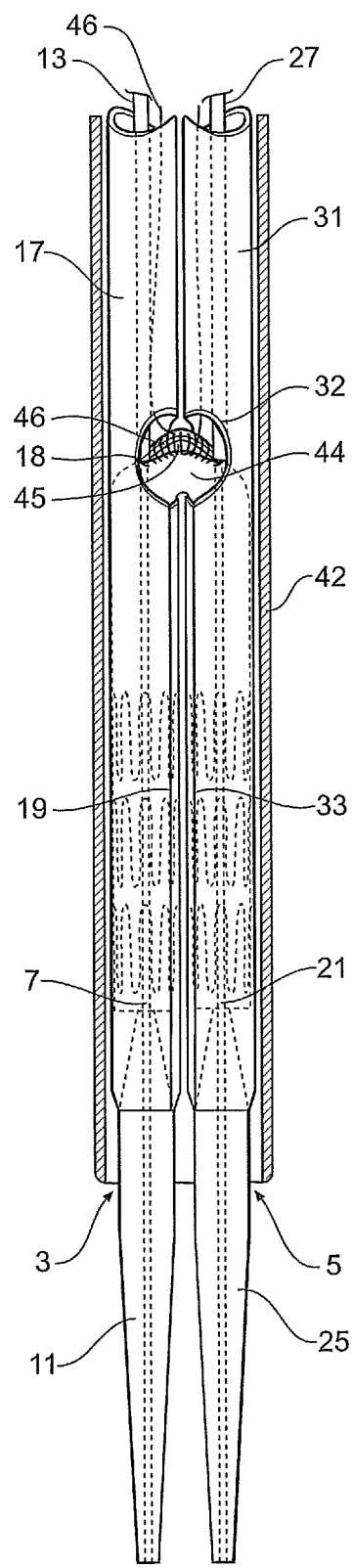
FIG. 6 shows a portion of a laparoscopic conduit mounted onto the delivery device of FIG. 1.

FIG. 6 shows detail of the proximal end of the laparoscopic delivery device of FIG. 1.

Sheath 42 encloses first introducer 3 and second introducer 5. The first introducer 3 has a nose cone dilator 11 mounted onto the guide wire catheter 7 which extends from the pusher catheter 13. An inner sheath 17 encloses the catheters and a portion of the laparoscopic conduit 44. The second introducer 5 includes a pusher catheter 27 and guide wire catheter 21 extending to a dilator 25. A sheath 31 covers a portion of the laparoscopic conduit 44 and extends forward to the dilator 25. As will be apparent from FIG. 6, the dilators 11, 25 extend out of the proximal end of the sheath for deployment purposes.

The first and second inner sheaths 17 and 31 each have an aperture 18 and 32, respectively, through which the intermediate portion of the laparoscopic conduit 44 extends between the first and second introducers substantially in a U-shape. Extending from the respective apertures 18 and 32 are split lines 19 and 33 which extend to the proximal ends of the respective inner sheaths 17 and 31.

The guide wire catheters 7 and 21 extend out through an aperture 45 in the apex of the laparoscopic conduit 44. The aperture 45 is pre-stitched with one or more suture threads 46, such that after placement the suture thread can be pulled tight to close the aperture.

Figure 7:
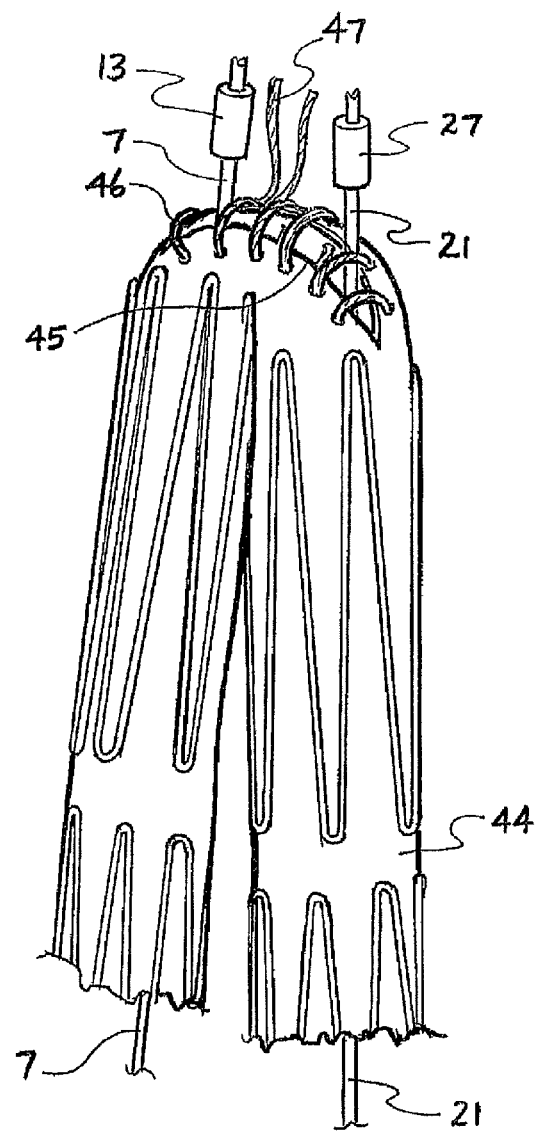
FIG. 7 shows a schematic view of the proximal end of the delivery device of FIG. 1.

FIG. 7 shows a further detail of the U-shaped portion of the laparoscopic conduit without the sheaths. It will be particularly noted that the first and second guide wires 7 and 21 pass out of the aperture 45 and the proximal ends of the pusher catheters 13 and 27 extend just to the laparoscopic conduit 44.

Figure 8:
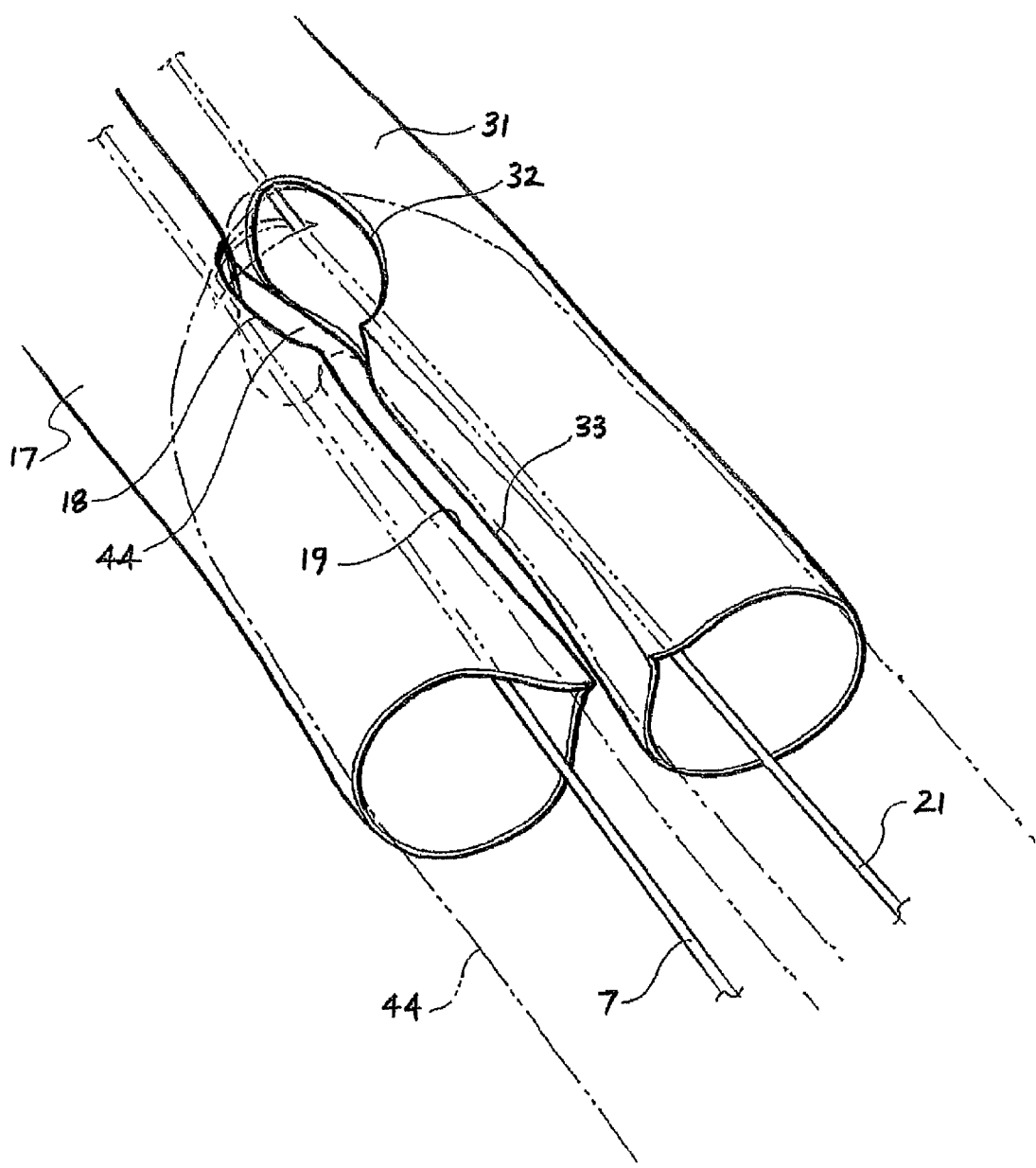
FIGS. 8 to 12 show further details of a splittable sheath being a component of the device of the laparoscopic conduit device and the various stages of it being split.

FIG. 8 shows a schematic view of the inner sheaths 17 and 31 with the laparoscopic conduit 44 extending between them. As each sheath is retracted the laparoscopic conduit 44 causes the splits 19 and 33 which commence at the apertures 18 and 32 to split open, thereby allowing the sheaths to be retracted past the laparoscopic conduit 44 which exits one aperture and enters the other.

Figures 9, 10:
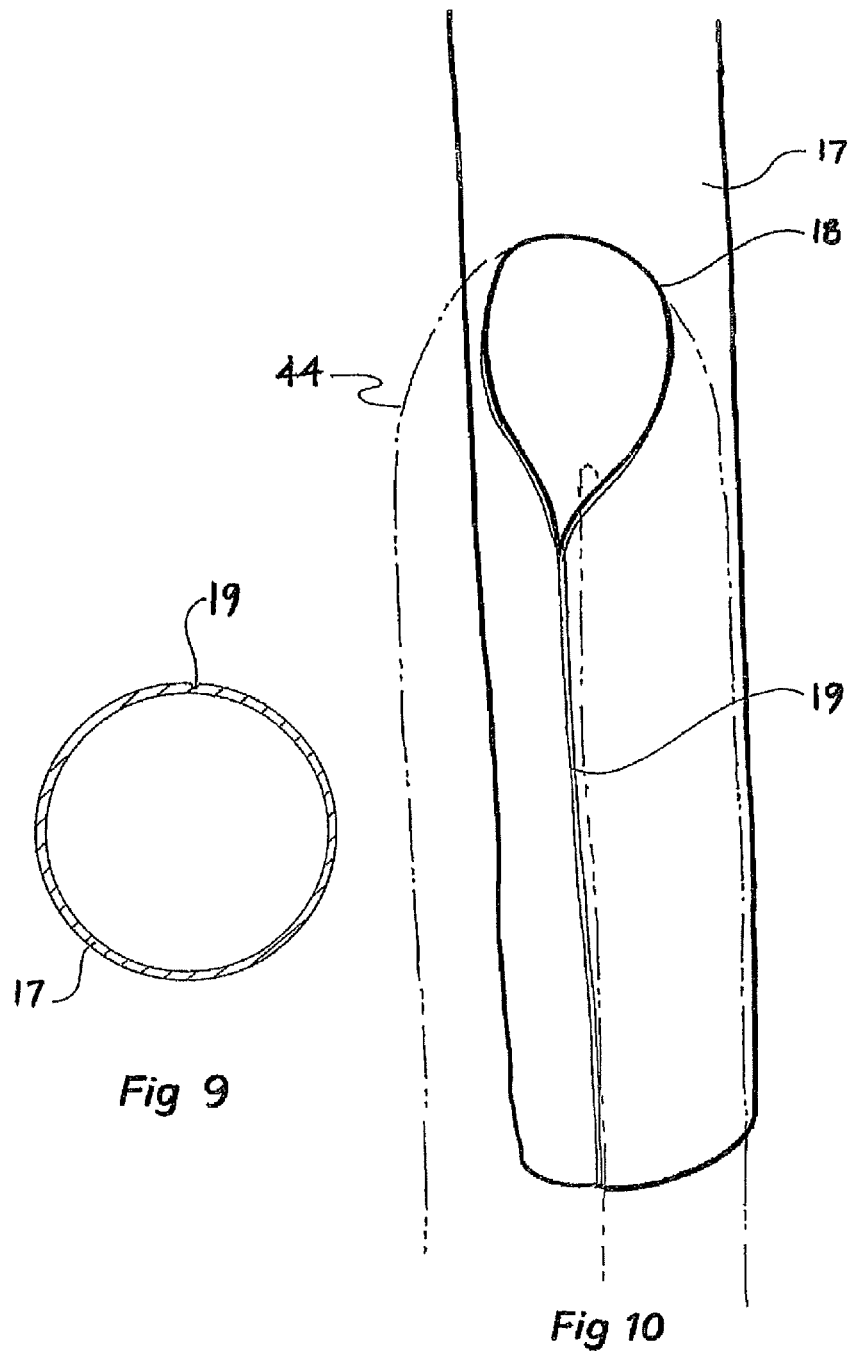

FIG. 9 shows detail of a sheath 17 with a line of weakening 19 which provides the line for splitting the sheath during retraction. The line of weakness is in this embodiment formed by a longitudinal line of reduced thickness in the wall of the sheath on one or both of the inner and outer surfaces of the sheath.

FIG. 10 shows a view of one of the sheaths and it will be noted that the aperture 18 is in a substantially tear drop shape pointing towards the line of weakness 19 to encourage splitting to occur as easily as possible when the sheath 17 is retracted from the laparoscopic conduit 44 while at the same time containing the laparoscopic conduit during the deployment procedures.

Figure 11:
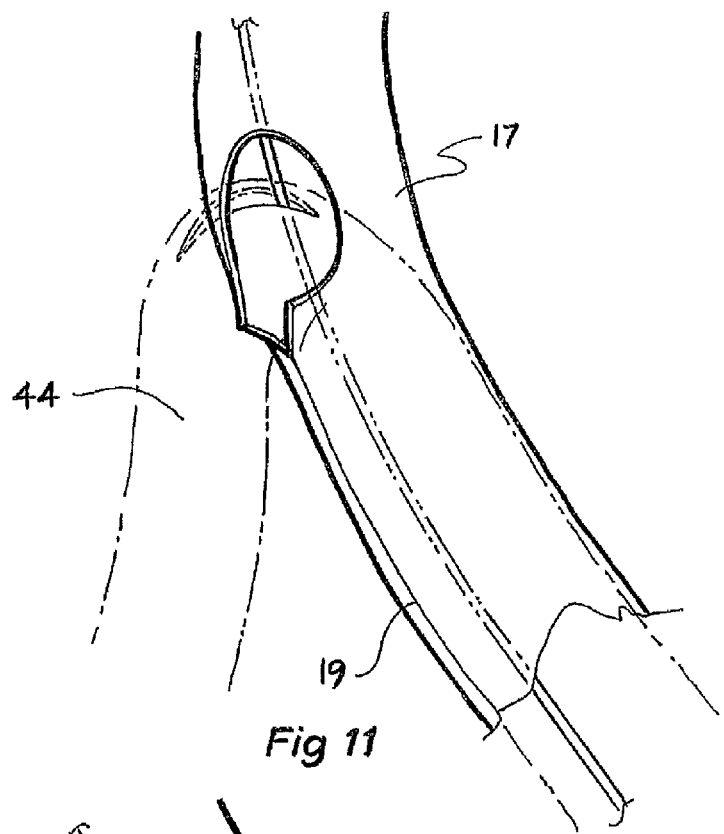
Figure 12:
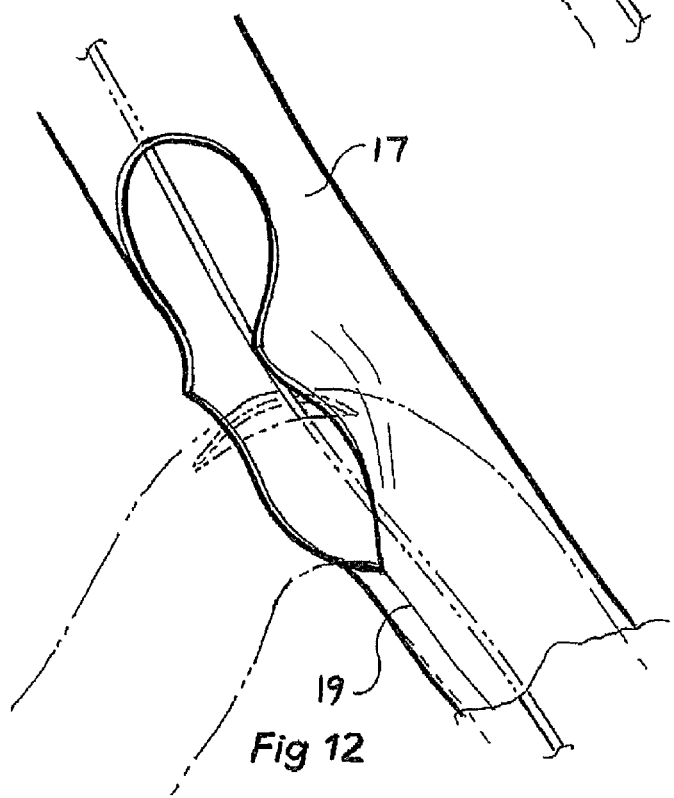

FIG. 11 shows commencement of propagation of the splitting of the sheath 17 along the split line 19 and FIG. 12 shows progress of the splitting of the sheath 17 along line of weakness 19.

Figure 13:
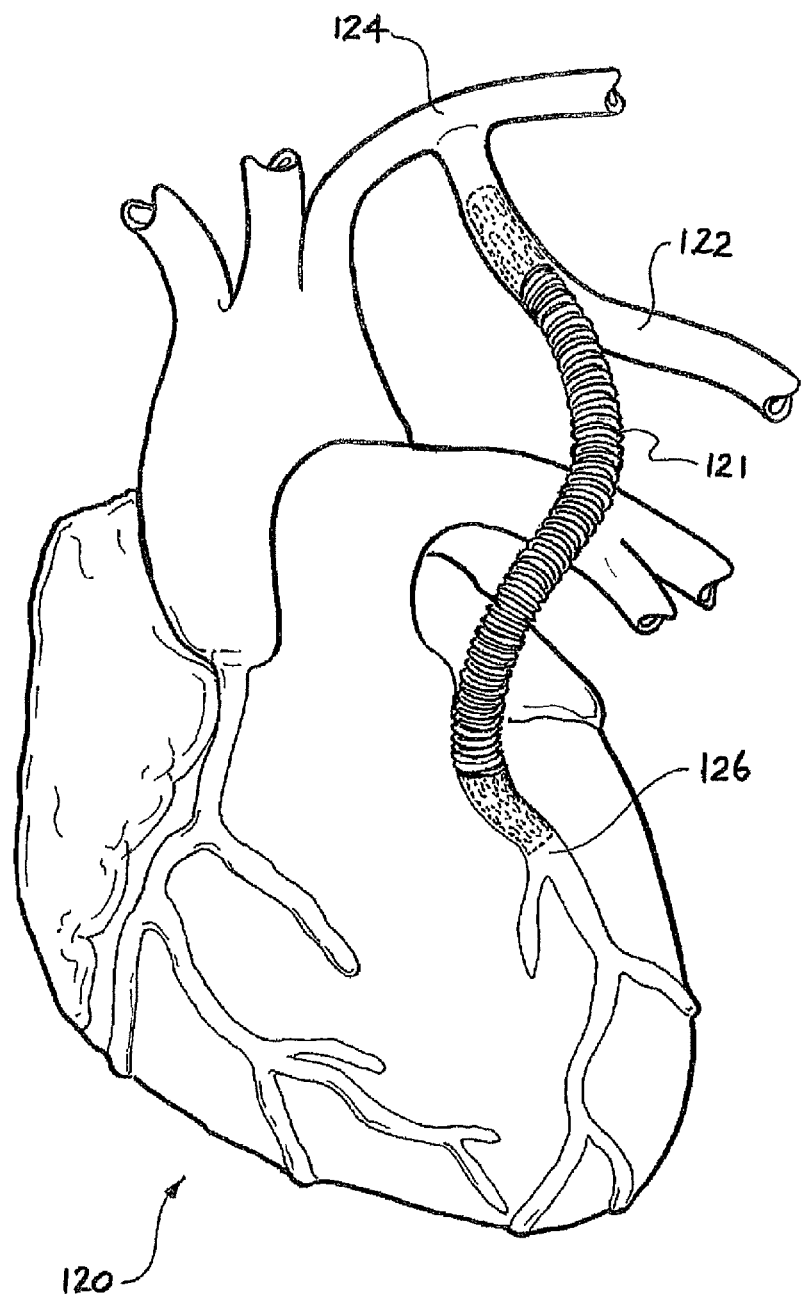
FIG. 13 shows an example of deployment of a laparoscopic conduit for coronary bypass using the delivery system of FIG. 1.

FIG. 13 shows a specific application of the endoscopic conduit system taught herein. In this drawing a heart 120 has an occlusion in the left coronary artery. A bypass has been deployed in a thoracoscopic operation between the internal thoracic artery 122, which extends from the left subclavian artery 124, to the left coronary artery 126 thereby bypassing the occlusion in the left coronary artery.

FIGS. 14 to 22 show the various stages of placement by endoscopic techniques of a laparoscopic conduit using the delivery device of FIGS. 1 and 6 to 12. The reference numerals will be the same as those used in relation to FIGS. 1 to 4 for corresponding items.

Figure 14:
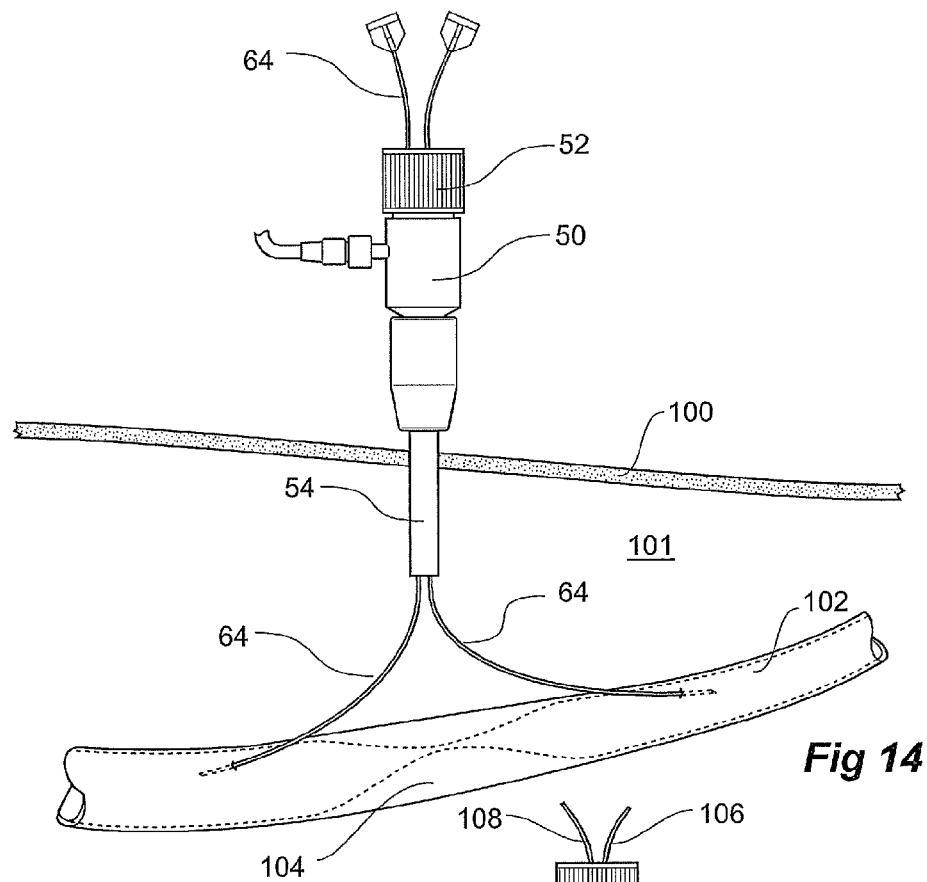
FIGS. 14 to 22 show the various stages of placement by endoscopic techniques of a laparoscopic conduit using the delivery device FIG. 1.

FIG. 14 shows an abdominal wall 100 of a patient through which there has been introduced the proximal end of a laparoscopic deployment device provided with a laparoscopic port 50. The process of insertion of the laparoscopic deployment device involves making a nick in the wall 100 with a scalpel or similar device and forcing the blunt end of the blunt obturator (see FIG. 2) with the laparoscopic port 50 mounted onto it through the nick such that the sheath 54 of the laparoscopic port 50 enters through the aperture formed in the abdominal wall. The blunt obturator is then removed, leaving the sheath 54 extending through the abdominal wall 100. Muscle in the abdominal wall will close around the sheath 54 and provide a good seal. The valve 52 is closed to assist with maintaining insufflation pressure within the body cavity.

Within the body cavity 101 is a vessel 102 which has an occlusion 104 to be bypassed. The vessel may for instance be an aorta or a coronary artery.

Two curved needles 64 are then introduced through the valve 52 and sheath 54 and are directed so that one needle enters vessel 102 at one side of the obstruction 104 and the other needle enters the vessel 102 at the other side of the obstruction.

Figure 15:
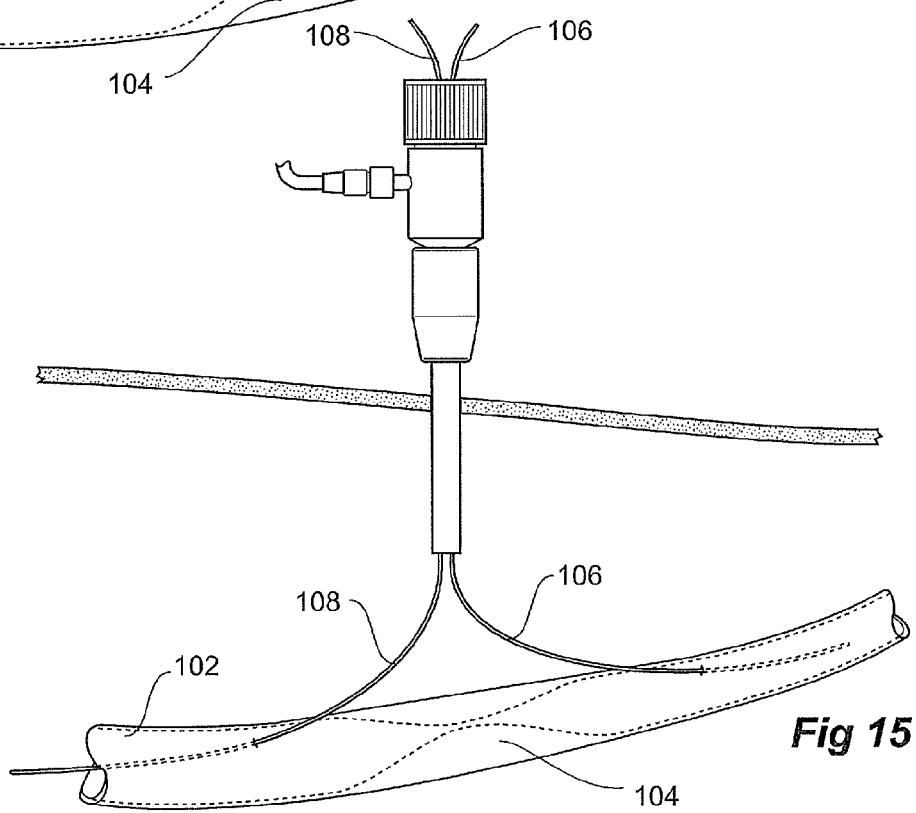

As shown in FIG. 15, guide wires 106 and 108 are then passed through the needles 64 so that they enter into the vessel 102 above and below the obstruction 104. The needles 64 are then removed, leaving the guide wires in place. The valve 52 is closed around the guide wires 106 and 108 to assist with maintaining insufflation pressure within the body cavity.

The placement of the needles and guide wires may be done sequentially so that one needle and then a guide wire is introduced to one side of the occlusion and then the other needle and guide wire are placed at the other side of the occlusion.

Figure 16:
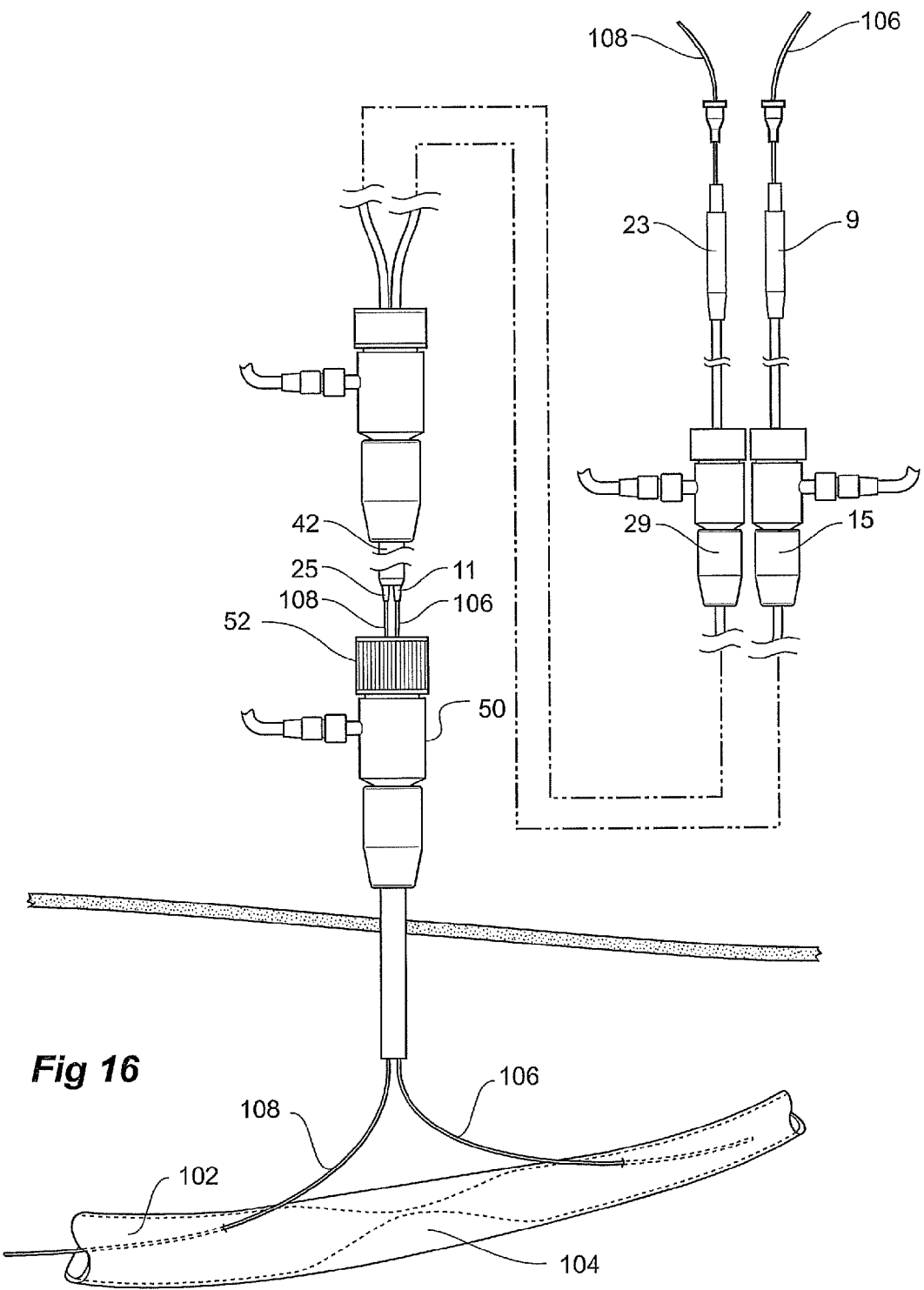

The laparoscopic delivery device 1 is then deployed onto the guide wires 106 and 108 from the distal ends thereof so that the dilator 11 slides over and follows guide wire 106 and dilator 25 slides over and follows guide wire 108. Both guide wires pass entirely through the delivery device to exit at the distal end of the device. This stage is shown in FIG. 16. The valve 52 is then opened to allow the nose cone dilators 11 and 25 and sheath 42 to enter into the port sheath and then the valve 52 is closed around the middle sheath 42.

Figure 17:
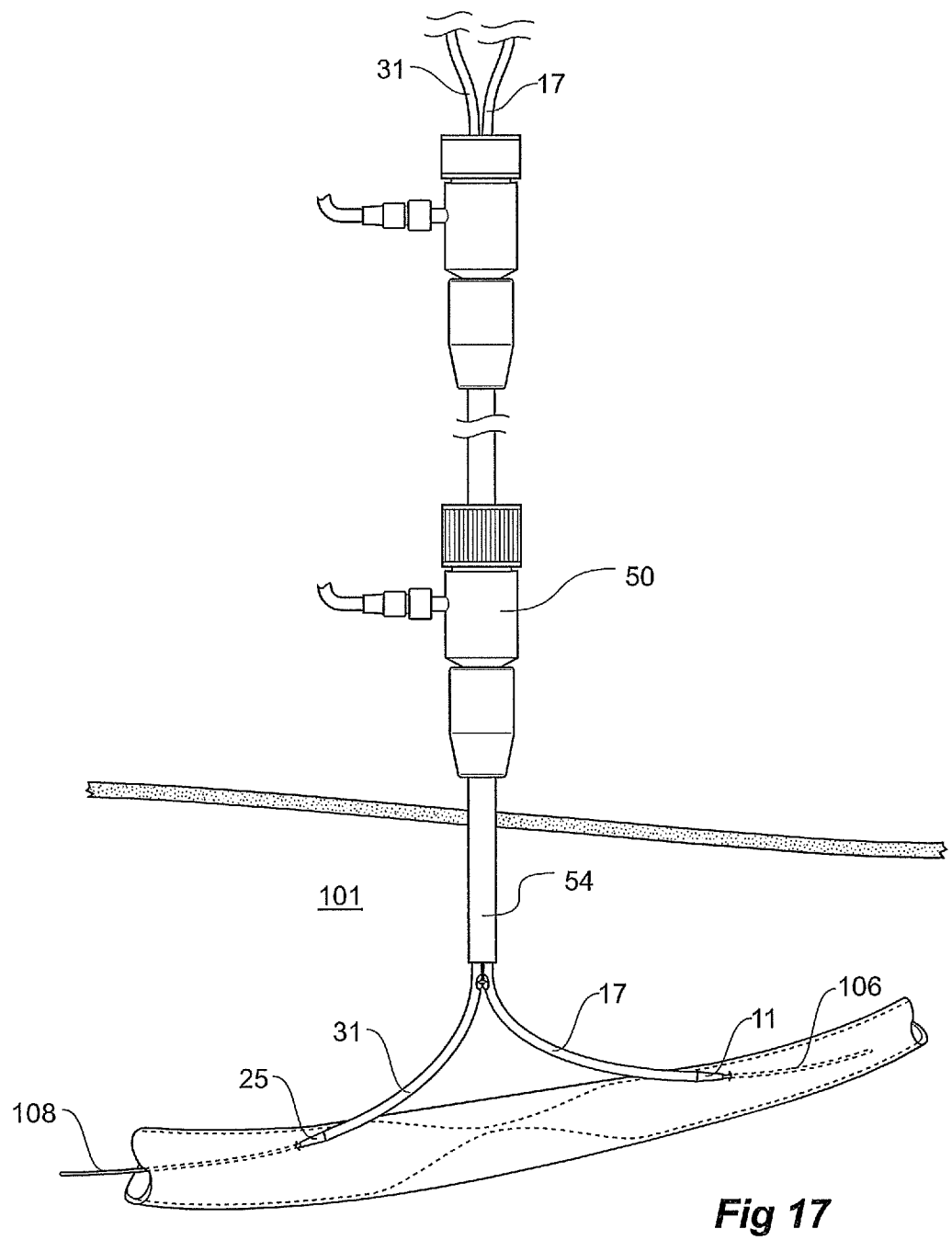

Next as shown in FIG. 17 the individual first and second pusher catheters 13 and 27 are advanced so that the respective first inner sheath 17 and second inner sheath 31 pass entirely through the laparoscopic port 50 and exit the sheath 54 within the body cavity 101 and continue to pass along the guide wires 106 and 108 until the respective dilators 11 and 25 abut the vessel wall.

Figure 18:
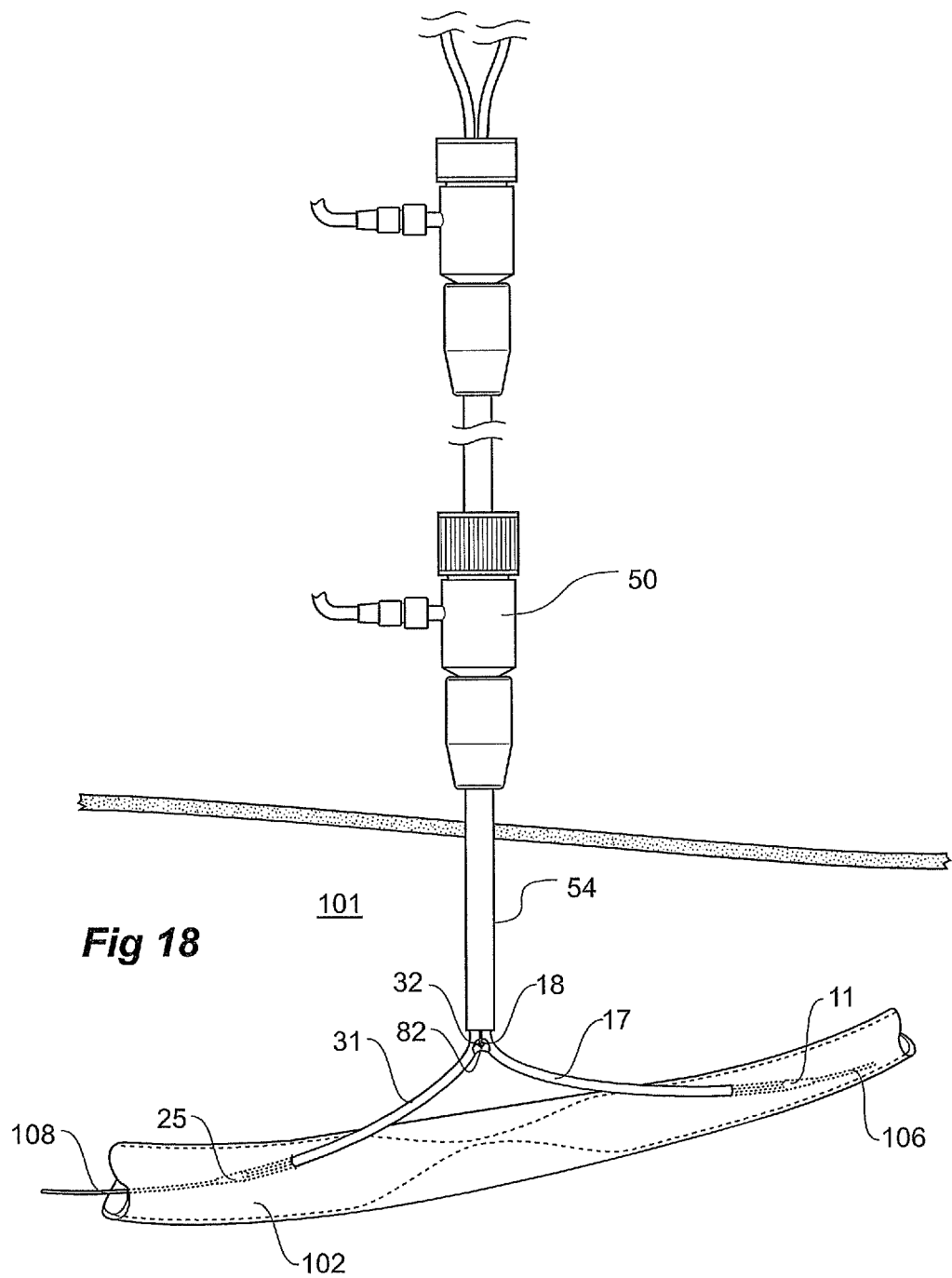

Continued advancement of the pusher catheters 13 and 27 causes the respective dilators 11 and 25 to enter the vessel 102 at the spaced apart locations and to extend some distance into the vessel in each direction. This stage is shown in FIG. 18. It will be noted that the intermediate portion 82 of the laparoscopic conduit 80 which is within the sheaths 17 and 31 can been seen where it passes out from the aperture 18 in the sheath 17 and into aperture 32 in the sheath 31.

Figure 19:
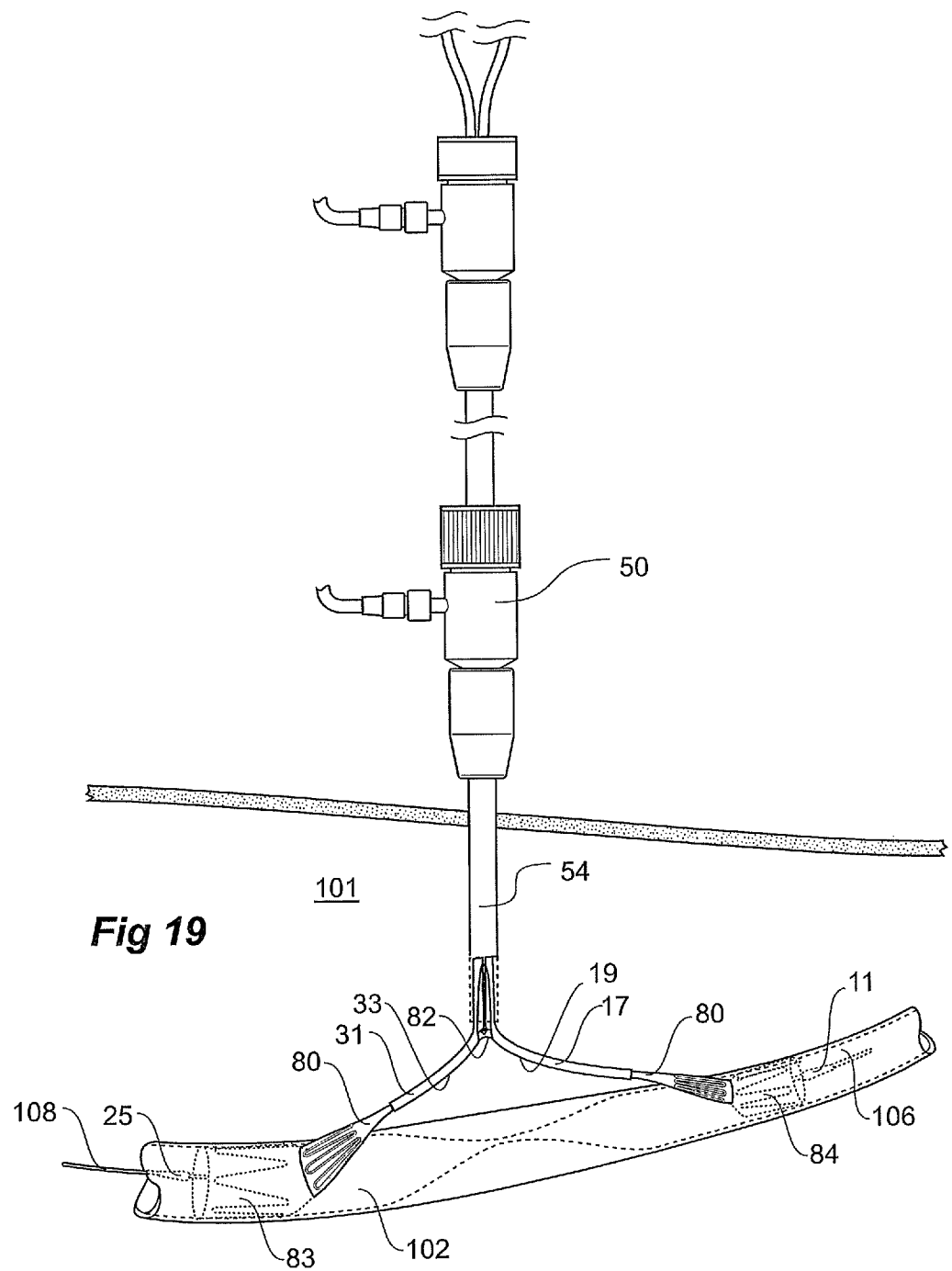

The sheaths 17 and 31 are then retracted by pulling on the hemostatic seal units 15 and 29, while holding the handles 9 and 23 (see FIGS. 1 and 16) to hold the first and second pusher catheters 13 and 27 stationary. This causes the sheaths 17 and 23 to split along the split lines 19 around the laparoscopic conduit 44 and to expose the first and second ends 83 and 84 of the laparoscopic conduit 80, as shown in FIG. 19. The first and second ends 83 and 84 of the laparoscopic conduit 80 have at least their first stents 85 positioned within the vessel 102 and preferably so that the gap between the first and second stents at each end is positioned at the entry aperture in the vessel.

Figure 20:
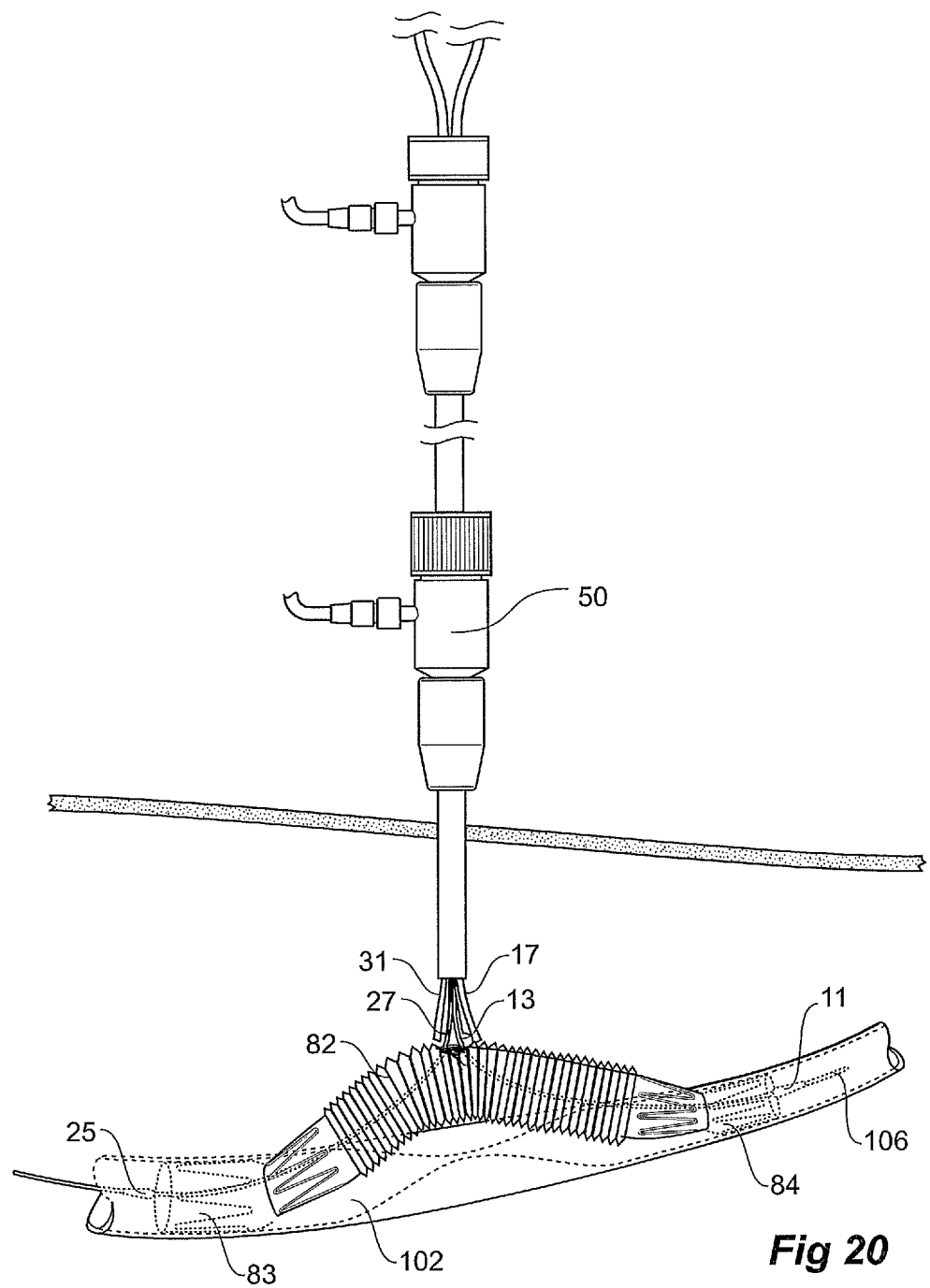

Retraction of the hemostatic seal units 15 and 29 while holding the handles 9 and 23 to hold the first and second pusher catheters 13 and 27 stationary continues until the sheaths 17 and 31 are completely split to their proximal ends and the guide wire catheters 7 and 21 extend through the aperture 87 in the central portion of the conduit 82. This stage is shown in FIG. 20.

Figure 21:
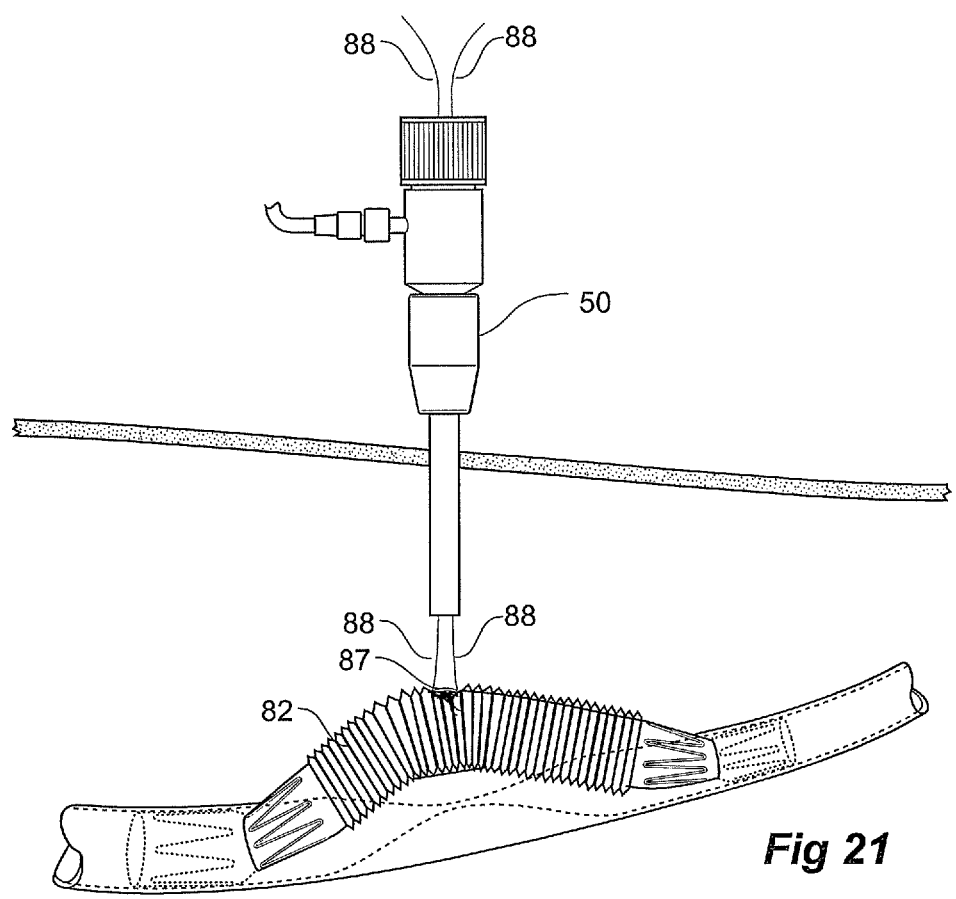

The first and second guide wire catheters 7 and 21 are then retracted as are the guide wires 106 and 108, leaving only in place threads 88 for the pre-stitched aperture 87. This stage is shown in FIG. 21.

The thread 96 is then pulled tight to close off the aperture 87, thereby sealing the corrugated portion closed. In many embodiments the suture thread will remain tight after having been pulled as a result of friction in the coupling, as is known in the art. It is envisaged that the nature thread could be provided with a self-tightening knot such as a Half-Blood knot. Knots of such a type are known in the art.

Figure 22:
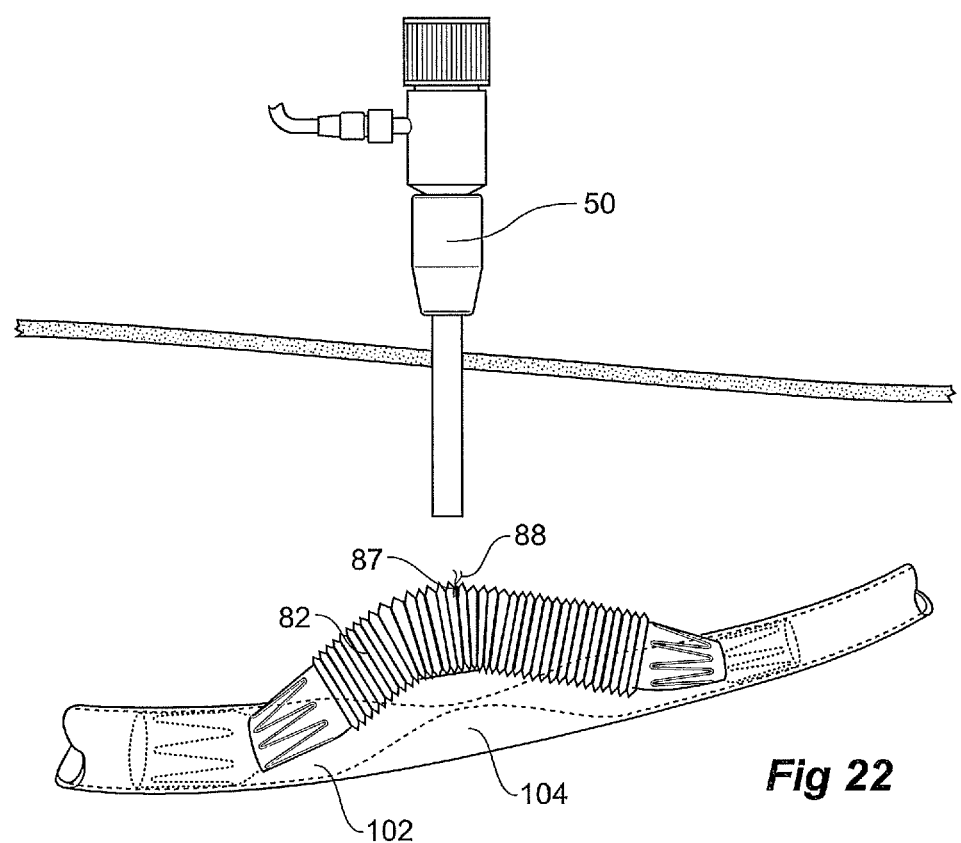

This sealing stage is shown in FIG. 22. The laparoscopic port 50 can then be removed.

It will be noted that by this process the occluded portion 104 of the vessel 102 has been bypassed using a laparoscopic conduit 80. The corrugated central portion 82 of the laparoscopic conduit is sufficiently self supporting to provide a blood flow path outside the vessel.

One embodiment of the invention and a method of use of the invention will now be discussed but the invention is not limited to this embodiment.

A kit of parts suitable for deployment of double ended laparoscopic bypass conduit can include:

Two curved hollow needles.
Two guide wires.
Laparoscopic port sheath with blunt obturator loaded into it. The Laparoscopic port sheath has a manually operable "Captor" access valve at its outside end.
Double ended laparoscopic conduit loaded onto a delivery device.

The laparoscopic conduit is a length of graft material with at least a pair of stents at each end and optionally a tubular corrugated body in between. Intermediate the ends it has a longitudinal or transverse slit with pre-placed stitches to close off the slit when pulled. One end can be smaller than the other. The stents are preferably self expanding stents.

The delivery device is a pair of inner introducers extending through an outer introducer sheath with an access valve. Each inner introducer has a nose cone dilator, a guide wire catheter and an introducer catheter extending back to a handle and a sheath. Each sheath has an access valve at its distal end. The sheath has a line of weakness extending back from its proximal end to a side aperture in the sheath.

When the laparoscopic stent graft conduit is loaded on the inner introducers the respective guide wire catheters extend through the longitudinal or transverse slit in the conduit and the aperture in the side of the sheath. The conduit is mounted in a U-shape so that both ends of the conduit extend forward to the respective nose cone dilators and the tubular bodies and stents are diametrically restrained by the respective sheaths.

Optionally, a stiffer guide wire and thin walled catheter is also included in the kit of parts.

Preferred Method of Operation for Deployment of Double Ended Laparoscopic Bypass Laparoscopic Conduit This operation is described generally as an endoscopic process but may be for thoracoscopic or laparoscopic operation. The operation is used to bypass an occlusion in an artery or other vessel, where there is some impassable pathology or where there is an aneurysm and the normal Seldinger access is unsuitable, for example due to impassable pathology. This operation enables the placement past an occlusion or damaged portion in a vessel such as an artery. A laparoscopic conduit is placed so that its ends are deployed into the vessel and opening away from the occlusion to allow blood flow past the occlusion. At times during the operation it may be necessary to clamp the vessel at least proximal of the occlusion.

A preferred practical method includes the following steps:

Make a small nick in the abdomen wall at the desired entry point.

Introduce the laparoscopic port sheath with a blunt obturator loaded into it through the nick and extend internally to adjacent the vessel as required for placement of one end of the double ended laparoscopic conduit. Withdraw the obturator.

Insert first curved needle with guide wire loaded into it through the access valve in the laparoscopic port sheath and puncture the vessel at the desired entry point and ensure that the curved needle is directed away from the occlusion in the vessel.

Extend the first guide wire through the needle and into the artery.

Remove the first curved needle.

Move distal end of laparoscopic port sheath to adjacent desired second entry point for other end of bypass while ensuring that first guide wire is not displaced.

Insert the second curved needle through the access valve in the laparoscopic port sheath and puncture the vessel at the desired second entry point.

Extend the second guide wire through the needle and into the vessel and ensure that the curved needle is directed away from the occlusion in the vessel.

Remove the second curved needle.

Optionally replace the first and/or second guide wires with stiffer guide wires. This can be done by deploying a thin walled catheter through the laparoscopic port sheath and over the guide wire and into the artery, removing the more flexible guide wire, extending the stiffer guide wire through the thin walled catheter and into the artery and then removing the thin walled catheter leaving the stiffer guide wire in place.

Deploy the double ended laparoscopic conduit loaded onto a modified Zenith delivery device by feeding the first and second guide wires into the guide wire lumens of the pair of nose cones extending from the distal end of the modified Zenith delivery device and so that the nose cones enter into the access valve of the laparoscopic port sheath.

Continue advancement of the double ended laparoscopic conduit loaded onto the delivery device until the respective nose cone commence tracking in opposite directions along the first and second guide wires.

Withdraw the outer sheath on the delivery device so the separate inner introducer catheters are free to continue tracking down the respective guide wires until the nose cones on the inner introducer catheters act as obturators to open up the respective vessel apertures to allow the inner introducer catheters into the vessel in two spaced apart places (eg above and below the occlusion etc).

Ensure that the gap between the first and second stents or the second and third stents at each end of the laparoscopic conduit are positioned at the respective apertures in the vessel wall.

Release the laparoscopic conduit ends mounted on the inner introducer catheters by withdrawing the sheaths of the inner introducer catheters. The sheaths have a line of weakness and split from the apertures in their sides where the conduit passes from the first inner introducer catheter in the U-shape into the second inner introducer catheter.

When the split sheaths are fully retracted into the laparoscopic port sheath then the first and second inner introducer catheters and dilators can be withdrawn through the intermediate slit in the stent graft conduit. If necessary the vessel at least proximal of the operation can be clamped to prevent blood loss until the slit is sewn up.

Sew up the slit using the pre-placed stitches.

Withdraw the guide wires and then the laparoscopic port sheath.

Note: At some stages in the operation it may be necessary to clamp the blood vessel at least proximally of the aneurysm to prevent blood loss until the aperture in the laparoscopic conduit has been closed off.

Throughout this specification various indications have been given as to the scope of the invention but the invention is not limited to any one of these but may reside two or more of these combined together. It will also be appreciated that although the preferred embodiment has been described in connection with laparoscopy, this embodiment and the teachings in this application are not limited to this particular medical application, as explained above.

What is claimed is:

1. A vascular bypass conduit for use in bypassing a portion of a patient's vasculature, the bypass conduit comprising:
   an elongate tube defined by a tubular wall of biocompatible graft material;
   the elongate tube having un-corrugated first and second ends comprising a plurality of self expanding stents therealong and a corrugated intermediate portion comprising no stents;
   a single aperture in the tubular wall of the corrugated intermediate portion;
   at least one suture thread pre-sewn in a loose manner into the aperture;
   at least a first introducer and a second introducer passing through the single aperture; and
   the bypass conduit being resiliently deformable substantially to a U-shape such that the aperture with the suture thread is open for the passage of the first introducer and the second introducer therethrough, whereby upon placement of the vascular bypass conduit in the patient the at least one suture thread can be used to close off the single aperture; and
   wherein the un-corrugated first and second ends each comprise a first tubular body portion that is straight and attached to the corrugated intermediate portion, a second tubular body portion that is flared and attached to the first tubular body portion, and a third tubular body portion that is straight and attached to the second tubular body portion.

2. The vascular bypass conduit as in claim 1, wherein at least one of the plurality of self-expanding stents at the first end and at the second end of the bypass conduit is located on the inside of the tubular wall and the other stent or stents of the plurality of stents are located on the outside of the tubular wall.

3. The vascular bypass conduit as in claim 1 wherein the aperture in the tubular wall of the corrugated intermediate portion is a longitudinal aperture.

4. The vascular bypass conduit as in claim 1 wherein the aperture in the tubular wall of the corrugated intermediate portion is a transverse aperture.

5. A vascular bypass conduit for use in bypassing a portion of a patient's vasculature, the bypass conduit comprising:
an elongate tube defined by a tubular wall of biocompatible graft material;
the elongate tube having un-corrugated first and second ends comprising a plurality of balloon expandable stents therealong and a corrugated intermediate portion comprising no stents;
a single aperture in the tubular wall of the corrugated intermediate portion;
at least one suture thread pre-sewn in a loose manner into the aperture;
at least a first introducer and a second introducer passing through the single aperture;
the bypass conduit being resiliently deformable substantially to a U-shape such that the aperture with the suture thread is open for the passage of the first introducer and the second introducer therethrough, whereby upon placement of the vascular bypass conduit in the patient the at least one suture thread can be used to close off the single aperture; and
wherein the un-corrugated first and second ends each comprise a first tubular body portion that is straight and attached to the corrugated intermediate portion, a second tubular body portion that is flared and attached to the first tubular body portion, and a third tubular body portion that is straight and attached to the second tubular body portion.

6. The vascular bypass conduit as in claim 5, wherein at least one of the plurality of balloon expandable stents at the first end and at the second end of the bypass conduit is located on the inside of the tubular wall and the other stent or stents of the plurality of stents are located on the outside of the tubular wall.

7. A vascular bypass conduit for use in bypassing a portion of a patient's vasculature, the bypass conduit comprising:
an elongate tube defined by a tubular wall of biocompatible graft material;
the elongate tube having un-corrugated first and second ends comprising a plurality of self expanding stents therealong and a corrugated intermediate portion comprising no stents;
a single aperture in the tubular wall of the corrugated intermediate portion;
at least one suture thread pre-sewn in a loose manner into the aperture;
at least a first introducer and a second introducer passing through the single aperture;
the bypass conduit being resiliently deformable substantially to a U-shape such that the aperture with the suture thread is open for the passage of the first introducer and the second introducer therethrough, whereby upon placement of the vascular bypass conduit in the patient the at least one suture thread can be used to close off the single aperture; and
wherein the un-corrugated first and second ends each comprise a first tubular body portion that is straight and attached to the corrugated intermediate portion, a second tubular body portion that is flared and attached to the first tubular body portion, and a third tubular body portion that is straight and attached to the second tubular body portion.

8. The vascular bypass conduit as in claim 7 wherein the aperture in the tubular wall of the corrugated intermediate portion is a longitudinal aperture.

9. The vascular bypass conduit as in claim 7 wherein the aperture in the tubular wall of the corrugated intermediate portion is a transverse aperture.

* * * * *